United States Patent [19]

Kirst et al.

[11] 4,424,344

[45] Jan. 3, 1984

[54] 2-N-ACYLATED AND 2-N-ALKYLATED DERIVATIVES OF 4-O-SUBSTITUTED-2-DEOXYSTREPTAMINE AMINOGLYCOSIDES AND PROCESS

[75] Inventors: Herbert A. Kirst; Brenda A. Truedell, both of Indianapolis, Ind.

[73] Assignee: Eli Lilly and Company, Indianapolis, Ind.

[21] Appl. No.: 304,292

[22] Filed: Sep. 21, 1981

Related U.S. Application Data

[63] Continuation-in-part of Ser. No. 189,440, Sep. 22, 1980, abandoned.

[51] Int. Cl.$^3$ ............................................. C07H 15/22
[52] U.S. Cl. .................................. 536/16.9; 536/16.8; 536/13.6; 536/16.6
[58] Field of Search .................. 536/17 R, 10, 13.6, 536/16.6, 16.8, 16.9

[56] References Cited

U.S. PATENT DOCUMENTS

| | | | |
|---|---|---|---|
| 4,002,608 | 1/1977 | Wright | 536/17 |
| 4,136,254 | 1/1979 | Nagabhushan et al. | 536/10 |
| 4,166,114 | 8/1979 | Igarashi | 424/180 |
| 4,169,197 | 9/1979 | Magerlein | 536/10 |
| 4,199,570 | 4/1980 | Igarashi et al. | 424/180 |
| 4,200,628 | 4/1980 | Igarashi et al. | 424/180 |
| 4,214,077 | 7/1980 | Carney et al. | 536/17 R |
| 4,230,847 | 10/1980 | Nagabhushan | 536/17 R |
| 4,283,528 | 8/1981 | Daniels et al. | 536/17 R |

FOREIGN PATENT DOCUMENTS 2036020 11/1978 United Kingdom .

OTHER PUBLICATIONS

H. A. Kirst, B. A. Truedell, and J. E. Toth, "Control of Site–Specific Substitution, etc.", *Tet. Letters,* vol. 22, p. 295 (1981, approximately the 1st quarter of the year).

Partial Program of 20th Interscience Conference on Antimicrobial Agents and Chemotherapy (Sep. 23, 1980).

J. Davies and S. O'Connor, "Enzymatic Modification of Aminoglycoside Antibiotics, etc.", *Antimicrob. Agents Chemother.,* 14, 69 (1978).

S. Umezawa et al., Tet. Letters, 4951 (1979).

O. Patil et al., Tet. Letters, 1035 (1978).

T. L. Nagabhushan et al., J. Am. Chem. Soc., 100, 5253 (1978).

T. L. Nagabhushan et al., Abst. 9th Int. Symp. Carbohyd. Chem., paper B36, B37, 1978.

R. E. Carney et al., Abstr. 175th ACS Meeting, Carb. 46, 1978.

G. Patil et al., Tet. Letters, 1031, 1978.

*Primary Examiner*—Blondel Hazel
*Attorney, Agent, or Firm*—Paul C. Steinhardt; Nancy J. Harrison; Arthur R. Whale

[57] ABSTRACT

Nickel salts are used to effect the regio-selective acylation and alkylation of the 2'-amino group of 4-O-substituted-2-deoxystreptamine containing aminoglycosides. The 2'-N-substituted derivatives of apramycin, certain α or β-(lower alkyl)aprosaminides and certain α or β-(substituted lower alkyl)aprosaminides are new. The 2'-N-substituted-4-O-substituted-2-deoxystreptamine aminoglycosides produced by the process of this invention are antibacterial agents.

37 Claims, No Drawings

2-N-ACYLATED AND 2-N-ALKYLATED DERIVATIVES OF 4-O-SUBSTITUTED-2-DEOXYSTREPTAMINE AMINOGLYCOSIDES AND PROCESS

CROSS-REFERENCE TO RELATED APPLICATION

This application is a continuation-in-part of application Ser. No. 189,440, filed Sept. 22, 1980 now abandoned.

BACKGROUND OF THE INVENTION

This invention relates to a process for the substantially regioselective acylation and alkylation of the 2'-amino group of 4-O-substituted 2-deoxystreptamine-containing aminoglycosides effected by nickel salts. Examples of 4-O-substituted 2-deoxystreptamine-containing aminoglycosides used in the process of the present invention include the antibiotics apramycin (see U.S. Pat. Nos. 3,691,279, 3,853,709 and 3,876,767):

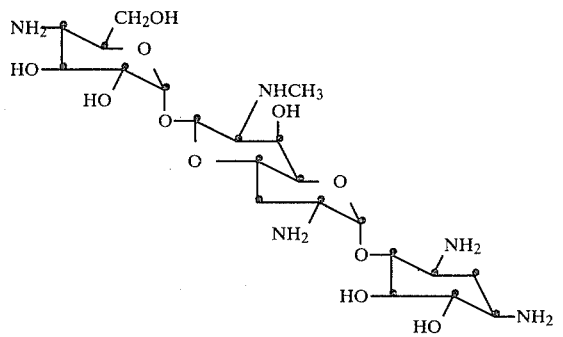

and nebramine:

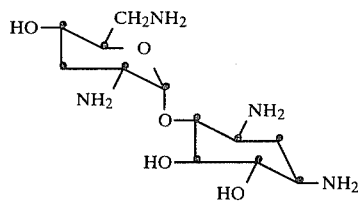

The nomenclature of the above formula of apramycin is simplified by the following numbering system in which the carbons of the 2-deoxystreptamine moiety are numbered 1 through 6, the carbons of the octose moiety are numbered with a single prime, 1'-8', and the carbons of the hexose moiety are numbered with a double prime, 1''-6''.

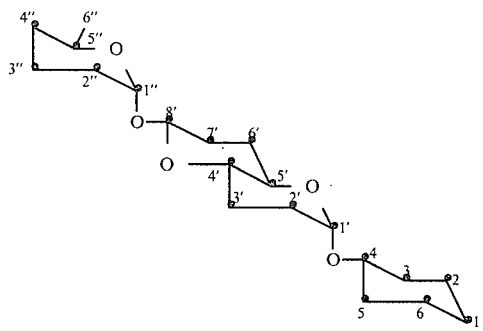

Analogously, the aprosaminide aminoglycosides referred to in this invention have the same numbering system as apramycin with respect to the octose and 2-deoxystreptamine moieties.

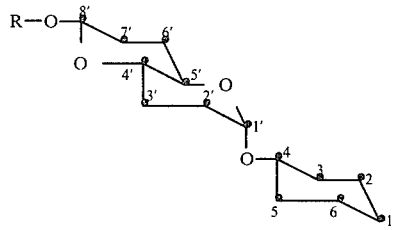

The numbering system for the pseudodisaccharides referred to in this invention, such as nebramine, has the carbons of the 2-deoxystreptamine moiety numbered 1-6 (the same as for apramycin and the aprosaminides), but the hexose carbons are numbered with a single prime, 1'-6'.

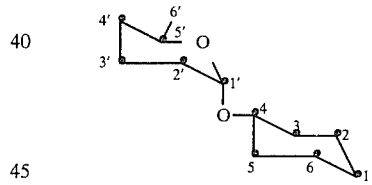

N-substituted derivatives of aminoglycoside antibiotics have been of great interest because many exhibit much broader antibacterial activity than do the parent antibiotics. Methods for selective N-substitution of aminoglycosides are, therefore, in great demand. The use of transition metal cations to selectively protect certain amino groups in aminoglycoside antibiotics from acylation has been reported by the following groups of workers:

T. L. Nagabhushan, *Abstr. 9th Int. Symp. Carbohyd. Chem.*, papers B36 and B37 (1978); T. L. Nagabhushan, et al., *J. Am. Chem. Soc.*, 100, 5253 (1978); T. L. Nagabhushan, W. N. Turner and A. Cooper, U.S. Patents 4,136,254 (1979) and 4,230,847 (1980). S. Hanessian and G. Patil, *Tet. Letters,* 1031 and 1035 (1978).

R. E. Carney and J. B. McAlpine, *Abstr. 175th ACS Meeting,* Carb. 46 (1978).

R. E. Carney and S. Hanessian, U.S. Pat. No. 4,214,077 (1980).

T. Tsuchiya, Y. Takagi and S. Umezawa, *Tet. Letters,* 4951 (1979).

Although a number of different transition metal cations were examined in these studies, the site of acylation did not generally depend on the particular cation used.

Until now, the prior art has not disclosed a direct acylation of the 2'-amino group of aminoglycoside antibiotics. In contrast to the results obtained in the prior art, we have been able to directly synthesize 2'-N-substituted derivatives of 4-O-substituted 2-deoxystreptamine aminoglycosides in a single reaction, using nickel salts to substantially control the site of derivatization.

A further aspect of this invention involves the biologically active 2'-N-substituted derivatives of apramycin, substituted apramycins and alkyl aprosaminides which are synthesized by the process of this invention.

SUMMARY OF THE INVENTION

The process of this invention involves regioselective acylation or alkylation of the 2'-amino group of 4-O-substituted-2-deoxystreptamine aminoglycoside substrates. The instant process is carried out by adding an acylating agent or alkylating agent to a mixture of the aminoglycoside substrate and a $C_1$ to $C_{10}$ carboxylate salt of nickel (II) in an aqueous polar organic solvent, and stirring the mixture for the appropriate time at a temperature between about 0° C. to about 40° C.

The aminoglycoside substrates that are used in the process of this invention are selected from a group consisting of apramycin, $\alpha$ or $\beta$-($C_1$ to $C_6$ alkyl) aprosaminide, $\alpha$ or $\beta$-($C_2$ to $C_6$ hydroxyalkyl)aprosaminide, $\alpha$ or $\beta$-($C_2$ to $C_6$ protected aminoalkyl)aprosaminide, and $\alpha$ or $\beta$-($C_3$ to $C_6$ (protected amino)hydroxyalkyl)aprosaminide, lividamine, paromamine and the 6'-N-protected derivatives of nebramine, neamine, gentamine $C_1$, gentamine $C_{1a}$, gentamine $C_2$, gentamine $C_{2a}$ and gentamine $C_{2b}$. The acylating agents for use in the present invention are reactive derivatives of acyl moieties selected from the group consisting of $\gamma$-protected amino-$\alpha$-hydroxybutyryl, $\beta$-protected amino-$\alpha$-hydroxypropionyl, N-protected glycyl, N-protected 3-hydroxypyrrolidine-3-carbonyl, N-protected 3-hydroxyazetidine-3-carbonyl and N-protected 2-hydroxy-2-(azetidin-3-yl)acetyl. The alkylating agents used in the instant process are $C_2$ to $C_4$ alkyl bromide, $C_2$ to $C_4$ alkyl iodide, $C_3$ to $C_5$ allyl bromide, $C_3$ to $C_5$ allyl iodide, benzyl bromide, benzyl iodide, substituted benzyl bromide and substituted benzyl iodide.

Compounds of the present invention include the above-mentioned apramycin and the various $\alpha$ or $\beta$-aprosaminide compounds, all substituted on the 2'-amino group by the above-listed acyl or alkyl moieties. As isolated from the process of this invention, the acylated compounds have their 2'-N substituent in the protected amino or N-protected form. These derivatives in the protected amino and N-protected forms are intermediates claimed in the instant invention. Removal of all amino protecting groups from these protected acyl intermediates yields the corresponding 2'-N-acyl antibiotic compounds.

Similarly, as isolated from the process of this invention, the 2'-N-alkylated derivatives may be in the amino-protected intermediate form. Removal of the amino protecting groups from these intermediates yields the corresponding 2'-N-alkyl antibiotic compounds.

In addition, the above 2'-N-acyl antibiotic compounds can be converted into corresponding 2'-N-alkyl antibiotic compounds by the reduction of the acyl group to a methylene group.

The above 2'-N-substituted antibiotic compounds, both in the free base form and the pharmaceutically acceptable acid addition salt form, are also claimed as part of this invention.

DETAILED DESCRIPTION OF THE INVENTION

This invention is directed to 2'-N-acylated and 2'-N-alkylated derivatives of apramycin, $\alpha$ or $\beta$-($C_1$ to $C_6$ alkyl)aprosaminide, $\alpha$ or $\beta$-($C_2$ to $C_6$ hydroxyalkyl)aprosaminide, $\alpha$ or $\beta$-($C_2$ to $C_6$ aminoalkyl)aprosaminide, $\alpha$ or $\beta$-($C_2$ to $C_6$ protected aminoalkyl)aprosaminide, $\alpha$ or $\beta$-($C_3$ to $C_6$ aminohydroxyalkyl)aprosaminide, $\alpha$ or $\beta$-($C_3$ to $C_6$ (protected amino)hydroxyalkyl)aprosaminide, and the pharmaceutically acceptable acid addition salts of these compounds. The acyl substituent on the 2'-amino group of the above compounds is selected from a group consisting of $\gamma$-amino-$\alpha$-hydroxybutyryl, $\gamma$-protected amino-$\alpha$-hydroxybutyryl, $\beta$-amino-$\alpha$-hydroxypropionyl, $\beta$-protected amino-$\alpha$-hydroxypropionyl, glycyl, N-protected glycyl, 3-hydroxypyrrolidine-3-carbonyl, N-protected 3-hydroxypyrrolidine-3-carbonyl, 3-hydroxyazetidine-3-carbonyl, N-protected 3-hydroxyazetidine-3-carbonyl, 2-hydroxy-2-(azetidin-3-yl)acetyl and N-protected 2-hydroxy-2-(azetidin-3-yl)acetyl. Alkyl substituents on the 2'-amino group of the above compounds are selected from the group consisting of the $C_2$ to $C_4$ alkyl, $C_3$ to $C_5$ allyl, benzyl, substituted benzyl, and carbonyl-reduced derivatives of the above deprotected amino acyl substituents and N-deprotected acyl substituents, namely: 4-amino-2-hydroxybutyl, 3-amino-2-hydroxypropyl, 2-aminoethyl, 3-hydroxypyrrolidine-3-methylene, 3-hydroxyazetidine-3-methylene, 2-hydroxy-2-(azetidin-3-yl)ethyl.

In the above description of the invention, the term "$C_1$ to $C_6$ alkyl" means a branched or straight chain alkyl such as methyl, ethyl, n-propyl, i-propyl, n-butyl, i-butyl, sec-butyl, t-butyl, n-pentyl, $\alpha$-methylpentyl, n-hexyl and like groups.

Similarly, by the term "$C_2$ to $C_6$ hydroxyalkyl", we mean from one to three hydroxyl groups bonded to any carbon atom of a $C_2$ to $C_6$ alkyl chain, provided that no more than one oxygen atom is bonded to any single carbon atom of the alkyl chain. Examples of the hydroxyalkyl chains include: 2-hydroxyethyl, 2-hydroxy-n-propyl, 3-hydroxy-n-propyl, 1,3-dihydroxy-2-propyl, 2,4-dihydroxy-n-butyl, 3-hydroxy-2-methylpropyl, 2,4,5-trihydroxy-n-pentyl, 2,4-dihydroxy-n-pentyl, 2-hydroxy-4-methylpentyl, 5-hydroxy-n-hexyl, 4,5,6-trihydroxy-n-hexyl, and like groups.

By the term "$C_2$ to $C_6$ aminoalkyl", we mean from one to three amino groups bonded to any carbon atom of a $C_2$ to $C_6$ alkyl chain, provided that no more than one heteroatom is bonded to any single carbon atom of the alkyl chain. Examples of these aminoalkyl chains include: 2-aminoethyl, 2-amino-n-propyl, 3-amino-n-propyl, 1,3-diamino-2-propyl, 2,4-diamino-n-butyl, 3-amino-2-methylpropyl, 2,4,5-triamino-n-pentyl, 3-amino-n-pentyl, 2-amino-4-methylpentyl, 5,6-diamino-n-hexyl, 3-amino-n-hexyl, and like groups.

By the term "$C_2$ to $C_6$ protected aminoalkyl", we mean from one to three protected amino groups bonded to any carbon atom of a $C_2$ to $C_6$ alkyl chain, provided that no more than one heteroatom is bonded to any single carbon atom of the alkyl chain. Examples of these protected aminoalkyl chains include the example compounds listed above for the $C_2$ to $C_6$ aminoalkyl chains wherein each of the amino groups is substituted by N-protecting groups, and like compounds.

By the term "$C_3$ to $C_6$ aminohydroxyalkyl", we mean a $C_3$ to $C_6$ alkyl chain substituted at any carbon atom by one amino group and one hydroxyl group, or by two amino groups and one hydroxyl group, or by one amino group and two hydroxyl groups, provided that no more than one heteroatom is bonded to any single carbon atom of the alkyl chain. Examples of these aminohydroxyalkyl chains include: 2-hydroxy-3-amino-n-propyl, 1-hydroxy-3-amino-2-propyl, 2-hydroxy-4-amino-n-butyl, 1-hydroxy-4-amino-2-butyl, 2-hydroxy-5-amino-n-pentyl, 4,5-diamino-3-hydroxy-n-pentyl, 3,5-dihydroxy-4-amino-n-pentyl, 2-amino-3-hydroxy-4-methylpentyl, 2-hydroxy-6-amino-n-hexyl and like groups.

By the term "$C_3$ to $C_6$ (protected amino)hydroxyalkyl", we mean a $C_3$ to $C_6$ alkyl chain substituted at any carbon atom by one protected amino group and one hydroxyl group, or by two protected amino groups and one hydroxyl group, or by one protected amino group and two hydroxyl groups, provided that no more than one heteroatom is bonded to any single carbon atom of the alkyl chain. Examples of these (protected amino)—hydroxyalkyl chains include the examples listed above for the $C_3$ to $C_6$ aminohydroxyalkyl chains wherein each of the amino groups is substituted by N-protecting groups, and like compounds.

The terms "protected amino" and "N-protected" used in the above description refer to an amino group substituted with one of the commonly employed amino blocking groups that are compatible with the present reaction conditions. Representative suitable amino-blocking groups for the purpose of this invention are described by J. W. Barton in "Protective Groups in Organic Chemistry," J. F. W. McOmie, Ed., Plenum Press, New York, N.Y., 1973, Chapter 2 and T. W. Greene, "Protective Groups in Organic Synthesis," John Wiley and Sons, New York, N.Y., 1981, Chapter 7. Preferred amino blocking groups are the various alkoxycarbonyl and aryloxycarbonyl groups, with the most preferred amino blocking group being benzyloxycarbonyl.

By the term "pharmaceutically acceptable acid addition salts" we mean those formed by standard acid-base reactions between the appropriate aminoglycoside and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, stearic, salicylic, methanesulfonic, benzenesulfonic, sorbic, picric, benzoic, cinnamic and like acids.

By the term "$C_2$ to $C_4$ alkyl", we mean ethyl, n-propyl and n-butyl.

By the term "$C_3$ to $C_5$ allyl" we mean allyl, 2-methylallyl, 3,3-dimethylallyl, 3-methylallyl, and 2,3 dimethylallyl. Those skilled in the art will recognize that the latter two allyl substituents can exist in either the E or Z geometric isomers. In the present invention, it is understood that the allyl compounds can exist in the pure E or Z form, or as a mixture the two isomers.

By the term "substituted benzyl" we mean a benzyl moiety where the phenyl ring is substituted with one substituent selected from the group consisting of fluoro, chloro, bromo, iodo, methyl, methoxy and trifluoromethyl. This substitutent can be in either the ortho, meta or para positions. Examples of these substituted benzyl groups include para-chlorobenzyl, para-bromobenzyl, para-iodobenzyl, para-methylbenzyl, para-methoxybenzyl, para-trifluoromethylbenzyl, meta-fluorobenzyl, meta-bromobenzyl, meta-methylbenzyl, meta-methoxybenzyl, meta-chlorobenzyl, ortho-chlorobenzyl, ortho-iodobenzyl, ortho-methylbenzyl, ortho-methoxybenzyl, ortho-bromobenzyl, and the like.

Those skilled in the art will recognize that all of the above listed acyl substituents except glycyl and N-protected glycyl, and the corresponding reduced acyl substituents, namely: 4-amino-2-hydroxybutyl, 3-amino-2-hydroxypropyl, 3-hydroxypyrrolidine-3-methylene, 3-hydroxyazetidine-3-methylene, 2-hydroxy-2-(azetidin-3-yl)ethyl, as well as many of the substituents described by the terms "$C_1$ to $C_6$ alkyl", "$C_2$ to $C_6$ hydroxyalkyl", "$C_2$ to $C_6$ aminoalkyl", "$C_2$ to $C_6$ protected aminoalkyl", "$C_3$ to $C_6$ aminohydroxyalkyl" and "$C_3$ to $C_6$ (protected amino)hydroxyalkyl," can exist as optical isomers. These terms refer to either the individual R or S isomers or to equal or unequal mixtures of the R and S isomers at each of the asymmetric carbon atoms.

The process for preparing the above 2'-N-acylated and 2'-N-alkylated compounds is the other aspect of this invention. Specifically, this process substantially selectively acylates or alkylates the 2'-amino group of the following substrates:

apramycin, $\alpha$ or $\beta$-($C_1$ to $C_6$ alkyl)aprosaminide, $\alpha$ or $\beta$-($C_2$ to $C_6$ hydroxyalkyl)aprosaminide, $\alpha$ or $\beta$-($C_2$ to $C_6$ protected aminoalkyl)aprosaminide, $\alpha$ or $\beta$-($C_3$ to $C_6$ (protected amino)hydroxyalkyl)aprosaminide, lividamine, paromamine, and the 6'-N-protected derivatives of nebramine, neamine, gentamine $C_1$, gentamine $C_{1a}$, gentamine $C_2$, gentamine $C_{2a}$, and gentamine $C_{2b}$, by (1) combining the above aminoglycoside with about two to about six molar equivalents of a nickel salt of the formula:

in water;

(2) diluting the above mixture with between about two to about ten volumes of a polar organic solvent;

(3) adding between about one to about two molar equivalents of an acylating agent or between about five to about twenty molar equivalents of an alkylating agent then carrying out the reaction at a temperature between about 0° C. to about 40° C. for a period between about 0.5 to about 24 hours for acylation, and between about 15 hours to about 60 hours for alkylation.

The terms "$C_1$ to $C_6$ alkyl", "$C_2$ to $C_6$ hydroxyalkyl", "$C_2$ to $C_6$ protected aminoalkyl", "$C_3$ to $C_6$ (protected amino)hydroxyalkyl", "protected amino", and " . . . N-protected . . . " are as defined above for the compounds of the instant invention.

Three of the above-listed aminoglycoside substrates for the process of this invention, namely apramycin, lividamine and paromamine, are known compounds and therefore their synthesis or isolation can be found in the literature.

The pseudodisaccharides nebramine, neamine, gentamine $C_1$, gentamine $C_{1a}$, gentamine $C_2$, gentamine $C_{2a}$, and gentamine $C_{2b}$ are also known compounds and therefore their synthesis or isolation can also be found in the literature. These pseudodisaccharides can be converted to their 6'-N-protected derivatives which are required as substrates for the instant process by methods analogous to the procedure given in Example 4, Part A of the Experimental Section.

The various substituted α or β aprosaminide substrates listed above can be made by methods analogous to the procedure described by S. O'Connor, et al., *Journal of Organic Chemisty,* 41, 2087 (1976).

The acylating agents used in the instant process are also known in the art. Additional examples for converting the known carboxylic acid precursors into suitable acylating agents for the process of this invention are given in Preparations 1 and 2 in the Experimental Section.

As with the compounds claimed in the present invention, it will be recognized by those skilled in the art that certain of the acylating agents, except for the reactive derivative of N-protected glycyl, certain $C_1$ to $C_6$ alkyl chains and certain substituted $C_2$ to $C_6$ alkyl chains and $C_3$ to $C_6$ alkyl chains of the α or β substituted aprosaminide substrates can exist as optical isomers. For the purposes of the process of this invention, these moieties can be used as their pure R or S configurations or as mixtures of equal or unequal proportions of these two configurations at each of the asymmetric carbon atoms.

In the above description of the process of the instant invention, the formula:

$$Ni(X)_2$$

refers to a nickel salt wherein the nickel is in the formal (II) oxidation state, and X refers to a $C_1$ to $C_{10}$ carboxylate ligand. The term "$C_1$ to $C_{10}$ carboxylate" includes straight or branched chain aliphatic carboxylates, as well as aromatic carboxylates, with acetate being the preferred carboxylate. Exemplary nickel salts used in the instant process include:

Ni(acetate)$_2$
Ni(propionate)$_2$
Ni(hexanoate)$_2$
Ni(2-ethylhexanoate)$_2$
Ni(benzoate)$_2$
Ni(octanoate)$_2$
Ni(neodecanoate)$_2$.

Although not explicitly depicted in the above formula and examples, the nickel salts used in the process of this invention may be either anhydrous or hydrated.

The term "acylating agent", as used in the above description of the instant process, means a reactive derivative of a carboxylic acid which is capable in the instant process of coupling the acid to an amino group by an amide linkage. The carboxylic acids that are converted into reactive derivatives for use as acylating agents in the process of this invention are selected from a group consisting of γ-protected amino-α-hydroxybutyric acid, β-protected amino-α-hydroxypropionic acid, N-protected glycine, N-protected 3-hydroxypyrrolidine-3-carboxylic acid, N-protected 3-hydroxyazetidine-3-carboxylic acid, and N-protected 2-hydroxy-2-(azetidin-3-yl)acetic acid. Examples of reactive derivatives of a carboxyl group are an acid halide, an acid anhydride, an activated ester, an acid azide and the like. Preferred reactive derivatives are acid anhydrides and activated esters, with the more preferred reactive derivatives being acid anhydrides and the activated esters formed with N-hydroxysuccinimide and N-hydroxyphthalimide.

After the 2'-N-(N-protected and amino-protected) acyl derivative compounds have been prepared by the instant process, they can be converted to the corresponding 2'-N-acyl antibiotic compounds by removal of all amino protecting groups from the acylated intermediate, using procedures well known in the art.

Furthermore, the above 2'-N-acyl antibiotic compound may have their carbonyl groups reduced to methylene groups with diborane or lithium aluminum hydride to yield the corresponding 2'-N-alkyl antibiotic compounds. Methods for reducing the carbonyl groups are well known in the art, and include methods such as the ones described by K. Igarashi, et al. in U.S. Pat. No. 4,201,774, herein incorporated by reference. An additional reference for the above reduction procedure is K. Richardson et al., *J. Antibiotics,* 30, 843 (1977).

The alkylating agents used in the instant process are $C_2$ to $C_4$ alkyl bromide, $C_2$ to $C_4$ alkyl iodide, $C_3$ to $C_5$ allyl bromide, $C_3$ to $C_5$ allyl iodide, benzyl bromide, benzyl iodide, substituted benzyl bromide and substituted benzyl iodide. The preferred alkylating agents are ethyl iodide, n-butyl bromide, n-butyl iodide, allyl bromide, allyl iodide, and benzyl bromide.

It should be noted that the instant process will result in the 2',6'-di-N-acylation or alkylation of nebramine, neamine, gentamine $C_1$, gentamine $C_{1a}$, gentamine $C_2$, gentamine $C_{2a}$, and gentamine $C_{2b}$ when the 6'-amino group of these substrates is not protected. Therefore, in order to acylate or alkylate the above pseudodisaccharide substrates on the 2'-amino group only, it is necessary to block the 6'-amino group with a suitable amino protecting group as defined above. This protecting group can then be removed after the 2'-amino group is substituted to yield the desired aminoglycoside derivative. An example of a 6'-N protection→2'-N substitution→6'-N deprotection procedure is given in Example 4 of the Experimental Section.

The first step of the instant process involves forming the nickel salt:aminoglycoside complex. This step is accomplished by mixing the aminoglycoside substrate compound and the nickel salt in water. Thorough mixing of these two components in the water is crucial and can be accomplished by employing methods such as sonication, vigorous stirring and mixing, moderate warming, etc. An aqueous solution is usually obtained; if not, a thoroughly mixed or dispersed suspension is sufficient. Between about a 2:1 to about a 6:1 molar ratio of nickel salt:aminoglycoside substrate can be used, with the usual ratio employed being about 4:1.

The second step of the instant process entails diluting the above mixture with a polar, organic solvent. By the term "polar organic solvent" we mean a solvent such as formamide, dimethylformamide, dimethylacetamide, dimethyl sulfoxide, hexamethylphosphoramide, t-butanol, tetrahydrofuran, acetonitrile, acetone, sulfolane, tetramethylurea, 2-pyrrolidinone, N-methylpyrrolidinone, dioxane, and the like, or a mixture of any of the above solvents, with the preferred solvent for acylation being dimethylformamide. The preferred "polar, organic solvent" for alkylation is also dimethylformamide. Between about 2 to about 10 volumes of polar, organic solvent per volume of water can be used, with the usual amount employed being about 5 volumes of organic solvent per volume of water. The resultant mixture is usually stirred for about five minutes to about one hour before proceeding to the next step. The mixture can be either heterogeneous or homogeneous at this point.

The final step of the instant process involves adding the appropriate acylating or alkylating agent to the mixture of step 2 of the process. The amount of acylating agent that can be used ranges from about a 1:1 to about a 2:1 ratio of acylating agent: aminoglycoside, with about a 1.5:1 ratio being typical. A ratio range of about 5:1 to about 20:1 of alkylating agent:aminoglycoside can be used, with the usual ratio employed being about 10:1.

The time required to complete the acylation in the final step is not critical. The acylation reaction can be stirred for a period ranging between about 0.5 to about 24 hours, with the usual time being about 15 hours. The alkylation reaction requires longer periods of time, encompassing a range of about fifteen hours to about sixty hours.

The temperature at which the instant process is carried out can range from between about 0° C. to about 40° C. Typically the reaction is run between about 20° C. to about 25° C.

Once the acylation reaction of the final step is completed, recognized isolation procedures may be utilized to obtain the desired purified product. One such procedure involves column chromatography on either silica gel or Chelex 100 resin (BioRad Labs, 2200 Wright Ave., Richmond, Ca. 94804) to adsorb the nickel salt from and separate the desired product from the resultant product mixture obtained from the instant process. To carry out this procedure, the solvent is evaporated in vacuo from the product mixture. The resultant residue is dissolved or suspended in an appropriate solvent and then loaded onto a column packed with the same solvent, using either Chelex 100 resin or silica gel as the stationary phase. An example of an appropriate solvent for use with the Chelex 100 resin is aqueous ammonium hydroxide. An example of an appropriate solvent for use with the silica gel is a 30:10:1 volume ratio of dichloromethane:methanol:ammonium hydroxide. The column is then eluted by common procedures (gradient or stepwise). The product can be chromatographed again on a second column of ion-exchange resin (e.g., Bio-Rex 70) or silica gel if necessary.

Chelex 100 is a styrene divinylbenzene copolymer functionalized with iminodiacetate ions which act as chelating ligands for binding metal ions.

Another isolation procedure removes Ni(II) ions by precipitation as the insoluble sulfide salts followed by ion-exchange chromatography to separate the desired products. Specifically, this procedure involves (a) evaporating the solvent from the product mixture, dissolving the resultant residue in dilute acid (e.g., 0.1 N HCl) and bubbling hydrogen sulfide gas through this mixture until precipitation of the nickel ion is complete, and (b) chromatographing the filtered solution from step (a) on an ion-exchange resin such as Bio-Rex 70 (BioRad Labs, supra) using an ammonium hydroxide solution or gradient to elute the desired product.

Bio-Rex 70 is a weakly acidic cation exchange resin containing carboxylic acid groups on a macroreticular acrylic polymer lattice. Similar useful ion-exchange resins are Amberlite CG-50 and Amberlite IRC-50 (Rohm and Haas Co., Philadelphia, Pa.).

The 2'-N-substituted aminoglycosides made by the process of this invention may be isolated in an intermediate form, wherein certain amino groups on the 2'-N-acyl substituent or on the aminoglycoside skeleton, or both, are protected. The amino-protected intermediates are converted to the corresponding 2'-N-substituted antibiotic compounds by removal of all of the amino-protecting groups, using methods well-known in the art. As described above, the 2'-N-acyl antibiotics may also be reduced to give the corresponding 2'-N-alkyl antibiotic compounds. These 2'-N-substituted antibiotic compounds, either in their free base form or their pharmaceutically acceptable acid addition salt form, are useful for treating infections in warm-blooded animals caused by gram-positive and gram-negative bacteria. These compounds can be administered parenterally, in the free base form or in the pharmaceutically acceptable acid addition salt form, using pharmaceutically acceptable formulations known in the art. These compounds can also be administered as veterinary compositions, such as, for example, in the feed or drinking water of farm animals to treat infections such as colibacillosis or swine dysentery.

Alternatively, these compounds can be used as a surface disinfectant. Solutions containing as little as 0.1 percent by weight of the antibiotic are effective for disinfecting purposes. Such solutions, preferably also containing a detergent or other cleansing agent, are useful for disinfecting objects such as glassware, dental and surgical instruments, and surfaces such as walls, floors, and tables in areas where maintenance of sterile conditions is important, i.e. hospitals, food-preparation areas, and the like.

The utility of the antibiotic compounds of this invention is illustrated by the following in vitro and in vivo test data obtained with representative compounds. In Table I, the minimum inhibitory concentration (MIC) for representative compounds against a wide range of gram-positive and gram-negative bacteria is presented. The MIC values were obtained by the standard agar dilution test.

TABLE 1

Antibiotic Activity of 2'-N—Substituted Derivatives of Apramycin and Nebramine vs. Gram-Positive and Gram-Negative Bacteria

| Test Organism* | Test Compound[1] Minimum Inhibitory Concentration (mcg/ml) | | | | |
|---|---|---|---|---|---|
| | 1 | 2 | 3 | 4 | 5 |
| Staphylococcus aureus X1.1 | 16 | 16 | 16 | 4 | 32 |
| Staphylococcus aureus V41 | 32 | 32 | 64 | 8 | 64 |
| Staphylococcus aureus X400 | 64 | 64 | 128 | 16 | 64 |
| Staphylococcus aureus S13E | 16 | 16 | 32 | 8 | 32 |
| Staphylococcus epidermidis EPI1 | 16 | 16 | 16 | 8 | 64 |
| Staphylococcus epidermidis EPI2 | 4 | 8 | 8 | 2 | 32 |
| Streptococcus pyogenes C203 | 32 | 32 | 64 | 16 | 128 |
| Streptococcus pneumoniae Park I | 32 | 32 | 128 | 16 | 128 |
| Streptococcus group D X66 | >128 | >128 | >128 | 128 | >128 |
| Streptococcus group D 9960 | >128 | >128 | >128 | >128 | >128 |
| Hemophilus influenzae C.L. | 64 | 32 | 16 | 16 | 64 |
| Hemophilus influenzae 76 | 32 | 32 | 32 | 16 | 64 |

TABLE 1-continued

Antibiotic Activity of 2'-N—Substituted Derivatives of Apramycin and Nebramine vs. Gram-Positive and Gram-Negative Bacteria

| Test Organism* | Test Compound[1] Minimum Inhibitory Concentration (mcg/ml) | | | | |
|---|---|---|---|---|---|
| | 1 | 2 | 3 | 4 | 5 |
| *Shigella sonnei* N9 | 32 | 32 | 16 | 8 | 64 |
| *Escherichia coli* N10 | 16 | 16 | 64 | 8 | 128 |
| *Escherichia coli* EC14 | 32 | 32 | 32 | 8 | >128 |
| *Escherichia coli* TEM | 8 | 8 | 8 | 2 | 32 |
| *Klebsiella pneumoniae* X26 | 8 | 8 | 8 | 4 | 64 |
| *Klebsiella pneumoniae* KAE | 16 | 32 | 16 | 8 | 64 |
| *Enterobacter aerogenes* X68 | 16 | 16 | 16 | 8 | 64 |
| *Enterobacter aerogenes* C32 | 16 | 16 | 16 | 8 | 64 |
| *Enterobacter aerogenes* EB17 | 16 | 32 | 16 | 8 | 64 |
| *Enterobacter cloacae* EB5 | 32 | 32 | 32 | 16 | 128 |
| *Enterobacter cloacae* 265A | 64 | 64 | 32 | 32 | >128 |
| *Salmonella heidelberg* X514 | 32 | 32 | 32 | 16 | 128 |
| *Salmonella typhimurium* 1335 | 16 | 32 | 64 | 8 | 128 |
| *Pseudomonas aeruginosa* X528 | 128 | 128 | 128 | 64 | >128 |
| *Pseudomonas aeruginosa* X239 | 64 | 128 | 64 | 64 | 128 |
| *Pseudomonas aeruginosa* Ps18 | 128 | 128 | 128 | 32 | 128 |
| *Serratia marcescens* X99 | 16 | 16 | 16 | 8 | 128 |
| *Serratia marcescens* SE3 | 32 | 32 | 32 | 16 | >128 |
| *Proteus morganii* PR15 | 128 | 128 | 128 | 32 | 64 |
| *Proteus inconstans* PR33 | 16 | 32 | 32 | 8 | 64 |
| *Proteus rettgeri* PR7 | 8 | 16 | 32 | 8 | 32 |
| *Proteus rettgeri* C24 | 16 | 16 | 16 | 8 | 64 |
| *Citrobacter freundii* CF17 | 32 | 32 | 64 | 16 | 64 |
| *Bordetella bronchiseptica* 16 | 128 | 128 | 128 | 32 | >128 |

*Numerals and letters following the names of test microorganisms refer to the strains.
[1]Test compounds numbered 1–5 are as follows:
1 = 2'-N—(S—γ-amino-α-hydroxybutyryl)apramycin
2 = 2'-N—(RS—γ-amino-α-hydroxybutyryl)apramycin(racemic side chain)
3 = 2'-N—glycylapramycin
4 = 2'-N—ethylapramycin
5 = 2'-N—(S—γ-amino-α-hydroxybutyryl)nebramine Table II illustrates the effective dose ($ED_{50}$, effective dose to protect 50 percent of the test animals) for representative compounds of this invention against an experimental bacterial infection in mice.

TABLE II

Subcutaneous Therapy of *Staphylococcus aureus* 3055 Infections in Mice

| Test Compound | Effective Dose ($ED_{50}$)* |
|---|---|
| 2'-N—(S—γ-amino-α-hydroxybutyryl)-apramycin | 6.5[1] |
| 2'-N—(RS—γ-amino-α-hydroxybutyryl)-apramycin[4] | 21.8[2] |
| 2'-N—glycylapramycin.HCl | 30[3] |
| 2'-N—ethylapramycin | <4.35[1] |
| 2'-N—(S—γ-amino-α-hydroxybutyryl)-nebramine | >70[3] |

*mg/kg × 2 subcutaneous doses at 1 and 5 hours post infection
[1]mice were challenged with 68.1 $LD_{50}$'s.
[2]mice were challenged with 331 $LD_{50}$'s.
[3]mice were challenged with 1,794 $LD_{50}$'s.
[4]Mixture of diastereomers The $ED_{50}$ values were determined as described by W. E. Wick et al., *Journal of Bacteriology*, 81 [No. 2], 233–235 (1961).

The following Examples (1–8) are provided to further illustrate this invention. Preparations 1 and 2 provide examples of methods for synthesizing activated esters used in the process of the present invention. It is not intended that this invention be limited in scope by reason of any of the preparations or examples. In the following preparations and examples, carbon-13 nuclear magnetic resonance spectra, field desorption mass spectra and optical rotations are abbreviated c.m.r., f.d.m.s., and o.r., respectively. The nuclear magnetic resonance spectra were obtained on either a Varian Associates FT-80 Spectrometer or a JEOL JNM-PS-100 Spectrometer using dioxane as the internal standard. The chemical shifts are expressed in δ values (parts per million downfield from tetramethylsilane). The field desorption mass spectra were taken on a Varian-MAT 731 Spectrometer using carbon dendrite emitters. Optical rotations were measured on a Perkin Elmer Model 241 Polarimeter. Thin layer chromatography was carried out on E. Merck silica gel plates.

PREPARATION 1

Preparation of N-(S-γ-Benzyloxycarbonylamino-α-hydroxybutyryloxy)succinimide

S-γ-Benzyloxycarbonylamino-α-hydroxybutyric acid (10.1 g, 40 mmol) and N-hydroxysuccinimide (4.60 g, 40 mmol) were dissolved in ethyl acetate (220 ml) and cooled in an ice bath. N,N'-Dicyclohexylcarbodiimide (8.25 g, 40 mmol) was added and the reaction mixture was stirred overnight. The resulting white precipitate was filtered and the filtrate was evaporated to dryness under reduced pressure. The residue was triturated with pentane (200 ml). The resultant white solid was filtered, washed with pentane and air-dried to yield 9.37 g (67%) of product. Crystallization from ethyl acetate yielded purified material, m.p. 108° C.

PREPARATION 2

Preparation of N-(N-Benzyloxycarbonylglycyloxy)succinimide

N-Benzyloxycarbonylglycine (10.9 g, 52.2 mmol) and N-hydroxysuccinimide (6.0 g, 52.2 mmol), were dissolved in dioxane (100 ml) and cooled in a cold water bath. N,N'-Dicyclohexylcarbodiimide (10.8 g, 52.2 mmol) was added and the mixture was stirred overnight. The white precipitate which formed was filtered, washed and air-dried (11.8 g, 100% of dicyclohexylurea). The filtrate was evaporated to dryness under reduced pressure, and the residual solid (16.2 g) was crystallized from ethyl acetate (50 ml) to give 8.4 g (53%) of crystalline N-(N-benzyloxycarbonylglycyloxy)succinimide, m.p. 110.5°–112° C.

EXAMPLE 1

Preparation of
2'-N-(S-γ-Amino-α-hydroxybutyryl)apramycin

Apramycin (1.08 g, 2.0 mmol) and nickel(II) acetate tetrahydrate (1.99 g, 8 mmol) were dissolved in water (20 ml) and this solution was diluted with dimethylformamide (100 ml). The resultant opaque, blue-green mixture was stirred for one hour at ambient temperature and then treated with N-(S-γ-benzyloxycarbonylamino-α-hydroxybutyryloxy)succimide (1.05 g, 3 mmol); a homogeneous green solution formed after about thirty minutes. After stirring overnight at ambient temperature, the solvent was evaporated under reduced pressure. The resultant residue was dissolved in a 30:15:2.5 mixture of dichloromethane:methanol:concentrated ammonium hydroxide and was loaded onto a silica gel column (Grace 950, 200 g) prewashed with the same solvent mixture. The column was successively eluted with three different mixtures of dichloromethane:methanol:concentrated ammonium hydroxide (30:15:2.5, 6:6:1, 3:3:1). The fractions containing the desired product were combined, the solvent was evaporated and the resultant colorless glassy residue was dissolved in water and was lyophilized to give 2'-N-(S-γ-benzyloxycarbonylamino-α-hydroxybutyryl)apramycin (0.60 g, 39% yield).

The above 2'-N-(S-γ-benzyloxycarbonylamino-α-hydroxybutyryl)apramycin (550 mg) was dissolved in a solution of water (30 ml), dioxane (10 ml) and glacial acetic acid (1 ml). 5% palladium on carbon (135 mg) was added and the mixture was hydrogenated at 45 p.s.i. for 24 hours at room temperature. The palladium catalyst was removed by filtration and the filtrate was evaporated to dryness. The residual glassy product was dissolved in water and loaded onto a column of Bio-Rex 70 (290 ml, ammonium hydroxide cycle, pH 10.0). This column was eluted with a linear gradient of 0.005 N ammonium hydroxide (1 l) and 0.5 N ammonium hydroxide (1 l) followed by continued elution with 0.5 N ammonium hydroxide. The fractions containing the desired product were combined, concentrated and lyophilized to yield 2'-N-(S-γ-amino-α-hydroxybutyryl)apramycin (383 mg, 84% yield): c.m.r. (D$_2$O-H$_2$O, pH ≧10) δ29.7, 32.9, 33.2, 36.3, 37.7, 48.8, 50.4, 51.0, 53.1, 61.6, 62.2, 66.1, 67.5, 70.5, 71.2, 71.7, 73.4, 74.2, 76.6, 78.3, 87.4, 95.4, 96.5, 98.5, 175.9; (at pH ≦2) δ29.0, 29.2, 31.1, 31.7, 37.6, 47.9, 50.0, 50.6, 53.0, 60.4, 61.2, 63.7, 67.7, 69.0, 70.1, 70.3, 70.6, 71.2, 73.4, 76.1, 78.8, 93.7, 95.3, 97.5, 175.5; f.d.m.s. m/e 623 (P+1-18); thin layer chromatography, R$_f$=0.14 using a 3:1:2 volume ratio of methanol:methylene chloride:concentrated ammonium hydroxide.

EXAMPLE 2

Preparation of
2'-N-(RS-γ-Amino-α-hydroxybutyryl)apramycin

The same procedure was followed as described in Example 1, except the acylating agent employed was N-(RS-γ-benzyloxycarbonylamino-α-hydroxybutyryloxy)succinimide (racemic mixture). The product obtained from this reaction, 2'-N-(RS-γ-amino-α-hydroxybutyryl)apramycin, had the following physical properties: c.m.r. (D$_2$O-H$_2$O, pH <3) δ29.3 (2x), 31.4, 31.9, 37.8, 48.0, 50.2, 51.0, 53.4, 60.6, 61.4, 64.0, 67.7, 69.2, 70.2, 70.3, 70.6, 71.3, 73.6, 76.2, (78.8 and 79.1 -doublet), 93.7, 95.3, 97.4, 175.6; f.d.m.s. m/e 641 (p+1); o.r. $[\alpha]_D^{25°}$ = +124.7° (H$_2$O, c=10 mg/ml).

EXAMPLE 3

Preparation of 2'-N-Glycylapramycin

Apramycin (2.16 g, 4 mmol) and nickel(II) acetate tetrahydrate (4.0 g, 16 mmol) were dissolved in water (40 ml) and the resultant solution was diluted with dimethylformamide (200 ml). To this mixture was added N-(N-benzyloxycarbonylglycyloxy)succinimide (1.84 g, 6 mmol). After stirring overnight at ambient temperature, solvent was evaporated under reduced pressure. The residue was dissolved in 0.1 N hydrochloric acid (250 ml) and a slow stream of gaseous hydrogen sulfide was bubbled into the mixture for one hour. After stirring overnight, the precipitate was filtered and the filtrate was evaporated to dryness under reduced pressure. The resultant residue was suspended in 1 N sodium hydroxide (35 ml) and was loaded on a column of 300 ml Bio-Rex 70 (ammonium hydroxide cycle, pH 10, pre-eluted with 0.01 N ammonium hydroxide). The column was eluted first with 0.01 N ammonium hydroxide (400 ml) and then with a linear gradient of 0.01 N ammonium hydroxide (2 l) and 0.05 N ammonium hydroxide (2 l). Fractions containing the desired product were located by thin layer chromatography, combined and lyophilized to yield 2'-N-(N-benzyloxycarbonylglycyl)apramycin (1.35 g, 46% yield).

The above 2'-N-(N-benzyloxycarbonylglycyl)apramycin was dissolved in a mixture of ethanol (100 ml), water (10 ml) and 1 N hydrochloric acid (10 ml). 5% palladium on charcoal (3 g) was added. This mixture was hydrogenated at 60 p.s.i. at ambient temperature overnight. The palladium catalyst was removed by filtration and the filtrate was placed in the refrigerator overnight. The desired crystalline 2'-N-glycylapramycin pentahydrochloride (1.01 g, 78% yield) precipitated from solution and was collected by filtration, washed with ethanol and air-dried: c.m.r. (D$_2$O-H$_2$O, pH ≧10) δ29.7, 32.8, 35.1, 44.2, 48.4, 50.3, 51.1, 53.1, 61.6, 62.1, 66.1, 67.4, 71.2, 71.7, 73.4, 74.2, 76.6, 77.4, 87.0, 95.4, 96.3, 98.5, 174.5; f.d.m.s. m/e 597 (P+1); o.r. $[\alpha]_D^{25°}$ = +127.3° (H$_2$O, C=8.3 mg/ml); thin layer chromatography, R$_f$=0.32 using a 3:1:2 volume ratio of methanol:methylene chloride:concentrated ammonium hydroxide.

EXAMPLE 4

A. Preparation of 6'-N-Benzyloxycarbonylnebramine

Nebramine (15.3 g, 50 mmol) was dissolved in water (400 ml) and tetrahydrofuran (THF) (150 ml). A solution of benzyloxycarbonylimidazole (11.6 g, 57 mmol) in THF (300 ml) was added dropwise over a 90 minute period and the reaction mixture was stirred overnight at ambient temperature. THF was evaporated under reduced pressure and the remaining aqueous solution was lyophilized. The resultant crude product was dissolved in water (100 ml) and loaded onto a column of 1500 ml Bio-Rex 70 (ammonium hydroxide cycle, pH 9.7). The column was eluted stepwise with 0.005 N ammonium hydroxide (1.5 l), 0.015 N ammonium hydroxide (2 l), 0.03 N ammonium hydroxide (5 l), and finally with 0.05 N ammonium hydroxide (10 l). The fractions eluted with 0.05 N ammonium hydroxide were analyzed by thin layer chromatography, and those containing the desired product were combined and lyophilized to give 6'-N-benzyloxycarbonylnebramine (9.7 g, 44% yield).

B. Preparation of 2'-N-(S-γ-Amino-α-hydroxybutyryl)nebramine

6'-N-Benzyloxycarbonylnebramine (880 mg, 2 mmol) and nickel(II) acetate tetrahydrate (1.99 g, 8 mmol) were dissolved in water (20 ml) and this solution was diluted with dimethylformamide (100 ml). To the resultant mixture was added N-(S-γ-benzyloxycarbonylamino-α-hydroxybutyryloxy)succinimide (1.05 g, 3 mmol). After stirring overnight at room temperature, the solvent was evaporated under reduced pressure, the residue was dissolved in methanol and the solvent was again evaporated to remove traces of dimethylformamide. The resultant residue was dissolved in a 30:10:1 mixture of dichloromethane:methanol:ammonium hydroxide and was loaded on a silica gel column (Grace 950, 90 g) prewashed with the same solvent mixture. The desired product was eluted from the column using the 30:10:1 mixture of dichloromethane:methanol:ammonium hydroxide as eluant. The fractions containing the desired product were combined and the solvent was evaporated. The residue was dissolved in a 1:1 mixture of water:dioxane, filtered and lyophilized to give 6'-N-benzyloxycarbonyl-2'-N-(S-γ-benzyloxycarbonylamino-α-hydroxybutyryl)nebramine (1.06 g, 79% yield).

6'-N-Benzyloxycarbonyl-2'-N-(S-γ-benzyloxycarbonylamino-α-hydroxybutyryl)nebramine (975 mg) was dissolved in a mixture of dioxane (20 ml), water (20 ml) and glacial acetic acid (1 ml). 5% palladium on charcoal (270 mg) was added and the mixture was hydrogenated at 40 p.s.i. overnight at ambient temperature. The palladium catalyst was removed by filtration and the filtrate was concentrated under reduced pressure and then loaded onto a column of 200 ml Bio-Rex 70 (ammonium hydroxide cycle, pH 8.6). After first eluting with a gradient of 0.005 N ammonium hydroxide (2 l) and 0.4 N ammonium hydroxide (3 l), the desired product was eluted with 0.5 N ammonium hydroxide. The fractions containing the desired product were combined and lyophilized to yield 2'-N-(S-γ-hydroxybutyryl)nebramine (397 mg, 70% yield): c.m.r. (D$_2$O-H$_2$O, pH $\geq$10) δ32.4, 33.3, 36.2, 37.7, 42.0, 48.8, 50.4, 51.0, 66.4, 70.5, 73.6, 76.7, 78.4, 86.3, 97.3, 175.9; f.d.m.s. m/e 408 (P+1); thin layer chromatography, R$_f$=0.23 using a 3:1:2 volume ratio of methanol:methylene chloride:concentrated ammonium hydroxide.

EXAMPLE 5

Preparation of 2'-N-Ethylapramycin

Apramycin (1.08 g, 2.0 mmol) and nickel(II) acetate tetrahydrate (1.99 g, 8.0 mmol) were dissolved in water (20 ml) and the solution was diluted with dimethylformamide (100 ml). The resultant opaque blue-green mixture was stirred for one hour at ambient temperature and then ethyl iodide (3.12 g, 20 mmol) was added. After stirring overnight at ambient temperature, solvent was evaporated under reduced pressure. The residue was suspended in a 30:10:1 mixture of methanol:dichloromethane:concentrated ammonium hydroxide (40 ml) and was loaded onto a silica gel column (Grace 950, 150 g) prewashed with the same solvent mixture. The column was eluted stepwise with eight different mixtures of methanol:dichloromethane:concentrated ammonium hydroxide [(a) 30:10:1 (400 ml), (b) 30:10:3 (430 ml), (c) 30:10:5 (900 ml), (d) 30:10:6 (460 ml), (e) 30:10:7 (1 l.) (f) 30:10:8 (400 ml), (g) 30:10:10 (400 ml), (h) 30:10:15 (400 ml)]. The fractions containing the desired product was combined, concentrated and lyophilized, yielding 785 mg of crude product. This material was dissolved in water, the solution's pH was adjusted to 8.8 and then the solution was loaded on a column of 300 ml Bio-Rex 70 (ammonium hydroxide cycle, pH 9.8, prewashed with 0.001 N ammonium hydroxide (1 l)). The column was eluted with a linear gradient of 0.01 N ammonium hydroxide (2 l.) and 0.10 N ammonium hydroxide (2 l). Fractions containing the desired product were combined and lyophilized, yielding 2'-N-ethylapramycin (150 mg, 13% yield): c.m.r. (D$_2$O-H$_2$O, pH $\geq$10) δ14.8, 30.8, 33.1, 36.8, 41.7, 50.4, 51.4, 53.5, 56.1, 61.8, 62.4, 66.3, 68.0, 71.4, 72.2, 73.8, 74.3, 76.9, 78.5, 88.5, 95.6, 96.4, 100.2; f.d.m.s. m/e 567 (P+); thin layer chromatography; R$_f$=0.25 using a 6:2:3 volume ratio of methanol:methylene chloride:concentrated ammonium hydroxide.

EXAMPLE 6

Preparation of 2'-N-(n-Butyl)apramycin

Method 1

Apramycin (54 mg, 0.1 mmol) was dissolved in water (1 ml). Nickel acetate tetrahydrate (100 mg, 0.4 mmol) was added and this solution was diluted with dimethylformamide (5 ml). The mixture was treated with 1-iodo-n-butane (0.115 ml, 1 mmol) and this reaction mixture was stirred at room temperature for 4 days. Thin layer chromatographic analysis (developed in 6:2:3 methanol:dichloromethane:ammonium hydroxide solution, visualized by chlorox spray and heating followed by starch-iodine spray reagent) of the reaction mixture showed 2'-N-(n-butyl)apramycin as the major product (R$_f$=0.35) along with unreacted apramycin (R$_f$=0.18). Bioautography of another thin layer chromatography plate against *B. subtilis* X12 showed a zone of inhibition due to 2'-N-(n-butyl)apramycin.

Method 2

The reaction of Method 1 was repeated using 1-bromo-(n-butane) (0.11 ml, 1 mmol) instead of 1-iodo-(n-butane). This reaction appeared to give a lower yield of the desired 2'-N-(n-butyl)apramycin than did the reaction of Method 1.

EXAMPLE 7

Preparation of 2'-N-Benzylapramycin

The reaction of Example 6, Method 1, was followed, except that benzyl bromide (0.06 ml, 0.5 mmol) was used instead of 1-iodo-n-butane. The reaction mixture was stirred at room temperature for 19 h, at which time thin layer chromatographic analysis showed 2'-N-benzylapramycin (R$_5$=0.32) to be the major product. Bioautography of a second thin layer chromatography plate against *B. subtilis* X12 showed a zone of inhibition due to 2'-N-benzylapramycin.

EXAMPLE 8

Preparation of 2'-N-Allylapramycin

Method 1

The reaction of Example 6, Method 1, was followed, except that allyl bromide (0.043 ml. 0.5 mmol) was used instead of 1-iodo-n-butane. The reaction mixture was stirred at room temperature for 22 h, at which time thin layer chromatographic analysis showed a substantial amount of 2'-N-allylapramycin ($R_f=0.27$) was present along with an unidentified material ($R_f=0.38$) and unreacted apramycin. Bioautography of a second thin layer chromatography plate against *B. subtilis* X12 showed a good zone of inhibition due to 2'-N-allylapramycin.

Method 2

The reaction of Method 1 above was repeated, except that allyl iodide (0.05 ml, 0.55 mmol) was used instead of allyl bromide. The reaction mixture was stirred at room temperature for 22 h, when thin layer chromatographic analysis of the reaction mixture gave the same results as in Method 1.

We claim:

1. A process for acylating or alkylating the 2'-amino group of a 4-O-substituted 2-deoxystreptamine aminoglycoside, comprising the steps of:
   (1) combining an aminoglycoside substrate selected from the group consisting of:
   apramycin, and $\alpha$ or $\beta$-($C_1$ to $C_6$ alkyl)aprosaminide, with about two to about six molar equivalents of a nickel salt of the formula:

$$Ni(X)_2$$

in water;
   (2) diluting the above aqueous mixture with between about two to about ten volumes of a polar organic solvent;
   (3) adding between about one to about two molar equivalents of an acylating agent or between about five to about twenty molar equivalents of an alkylating agent then carrying out the reaction at a temperature between about 0° C. to about 40° C. for a period between about 0.5 to about 24 hours for acylation or between about 15 hours to about 60 hours for alkylation, wherein:
   X is $C_1$ to $C_{10}$ carboxylate; wherein the acylating agent used is a reactive derivative of an acyl moiety selected from the group consisting of $\gamma$-protected amino-$\alpha$-hydroxybutyryl, $\beta$-protected amino-$\alpha$-hydroxypropionyl, N-protected glycyl, N-protected 3-hydroxypyrollidine-3-carbonyl, N-protected 3-hydroxyazetidine-3-carbonyl and N-protected 2-hydroxy-2-(azetidin-3-yl)acetyl; and the alkylating agents used are $C_2$ to $C_4$ alkyl bromide, $C_2$ to $C_4$ alkyl bromide, $C_2$ to $C_4$ alkyl iodide, $C_3$ to $C_5$ allyl bromide, $C_3$ to $C_5$ allyl iodide, benzyl bromide, benzyl iodide, substituted benzyl bromide and substituted benzyl iodide.

2. The process of claim 1, wherein the polar organic solvent is aqueous dimethylformamide.

3. The process of claim 1, wherein the nickel salt is nickel(II) acetate.

4. The process of claim 3, wherein the polar organic solvent is aqueous dimethylformamide.

5. The process of claim 1, wherein the acylating agent used is a reactive derivative of the acyl moiety $\gamma$-protected amino-$\alpha$-hydroxybutyryl.

6. The process of claim 5, wherein the acylating agent used is N-(S-$\gamma$-benzyloxycarbonylamino-$\alpha$-hydroxybutyryloxy)succinimide.

7. The process of claim 5, wherein the acylating agent used is N-(RS-$\gamma$-benzyloxycarbonylamino-$\alpha$-hydroxybutyryloxy)succinimide.

8. The process of claim 1, wherein the acylating agent used is a reactive derivative of the acyl moiety $\beta$-protected amino-$\alpha$-hydroxypropionyl.

9. The process of claim 1, wherein the acylating agent used is a reactive derivative of the acyl moiety N-protected glycyl.

10. The process of claim 9, wherein the acylating agent used is N-(N-benzyloxycarbonylglycyloxy)succinimide.

11. The process of claim 1, wherein the acylating agent used is a reactive derivative of the acyl moiety N-protected 3-hydroxypyrrolidine-3-carbonyl.

12. The process of claim 1, wherein the acylating agent used is a reactive derivative of the acyl moiety N-protected 3-hydroxyazetidine-3-carbonyl.

13. The process of claim 1, wherein the acylating agent used is a reactive derivative of the acyl moiety N-protected 2-hydroxy-2-(azetidin-3-yl)acetyl.

14. The process of claim 1, wherein the alkylating agent used is $C_2$ to $C_4$ alkyl bromide or $C_2$ to $C_4$ alkyl iodide.

15. The process of claim 14, wherein the alkylating agent used is n-butyl bromide or n-butyl iodide.

16. The process of claim 14, wherein the alkylating agent used is ethyl bromide or ethyl iodide.

17. The process of claim 1, wherein the alkylating agent used is $C_3$ to $C_5$ allyl bromide or $C_3$ to $C_5$ allyl iodide.

18. The process of claim 17, wherein the alkylating agent used is allyl bromide or allyl iodide.

19. The process of claim 1, wherein the alkylating agent used is benzyl bromide or benzyl iodide.

20. The process of claim 1, wherein the alkylating agent used is substituted benzyl bromide or substituted benzyl iodide.

21. The process of claim 1, wherein the aminoglycoside substrate is $\beta$-($C_1$ to $C_6$ alkyl)aprosaminide.

22. The process of claim 1, wherein the aminoglycoside substrate is apramycin.

23. The process of claim 22, wherein the alkylating agent used is $C_2$ to $C_4$ alkyl bromide or $C_2$ to $C_4$ alkyl iodide.

24. The process of claim 23, wherein the alkylating agent used is ethyl bromide or ethyl iodide.

25. The process of claim 23, wherein the alkylating agent used is n-butyl bromide and n-butyl iodide.

26. The process of claim 22, wherein the alkylating agent used is $C_3$ to $C_5$ allyl bromide or $C_3$ to $C_5$ allyl iodide.

27. The process of claim 26, wherein the alkylating agent used is allyl bromide or allyl iodide.

28. The process of claim 22, wherein the alkylating agent used is benzyl bromide.

29. The process of claim 22, wherein the acylating agent used is a reactive derivative of the acyl moiety N-protected glycyl.

30. The process of claim 29, wherein the acylating agent used is N-(N-benzyloxycarbonylglycyloxy)succinimide.

31. The process of claim 22, wherein the acylating agent used is a reactive derivative of the acyl moiety S-γ-protected amino-α-hydroxybutyryl.

32. The process of claim 31, wherein the acylating agent used is N-(S-γ-benzyloxycarbonylamino-α-hydroxybutyryloxy)succinimide.

33. The process of claim 22, wherein the acylating agent used is a reactive derivative of the acyl moiety of RS-γ-protected amino-α-hydroxybutyryl.

34. The process of claim 33, wherein the acylating reagent used is N-(RS-γ-benzyloxycarbonylamino-α-hydroxybutyryloxy)succinimide.

35. The process of claim 5, 6, 7, 9, 10, 14, 15, 16, 17, 18, 19, 22, 23, 24, 25, 26, 27, 28, 29, 30, 31, 32, 33 or 34, wherein the polar organic solvent is aqueous dimethylformamide.

36. The process of claim 5, 6, 7, 9, 10, 14, 15, 16, 17, 18, 19, 22, 23, 24, 25, 26, 27, 28, 29, 30, 31, 32, 33 or 34 wherein the nickel salt is nickel(II) acetate.

37. The process of claim 36, wherein the polar organic solvent is aqueous dimethylformamide.

* * * * *